United States Patent [19]

Marciel

[11] Patent Number: Plant 7,638

[45] Date of Patent: Sep. 3, 1991

[54] MINIATURE POT ROSE NAMED DEVAMARILLO

[75] Inventor: Stanley G. Marciel, Aptos, Calif.

[73] Assignee: DeVor Nurseries, Inc., Watsonville, Calif.

[21] Appl. No.: 529,314

[22] Filed: May 29, 1990

[51] Int. Cl.[5] ..... A01H 5/00

[52] U.S. Cl. ..... Plt./8

[58] Field of Search ..... Plt./8

*Primary Examiner*—James R. Feyrer

*Attorney, Agent, or Firm*—Charles W. Rummler

[57] ABSTRACT

A distinct variety of miniature pot rose plant particularly distinguished by its continuous and profuse production of relatively small blooms of a solid overall Cadmium Orange coloration born on strong, upright stems of a plant having an average height of about 23 cm. at twelve weeks of age in a 4 in. pot and a vigorous, free branching, upright growth habit with a moderate amount of foliage.

1 Drawing Sheet

BACKGROUND OF THE NEW PLANT

This new variety of pot rose plant originated as a seedling hybrid developed by me at Watsonville, Calif. by my crossing an unnamed and unpatented plant, selected from my collection of rose plants maintained at Watsonville for breeding purposes, with pollen from an unpatented variety named 'Amber Flash'. The present seedling was selected for propagation because of its profuse production of Cadmium Orange colored blossoms born on upright stems of a strong bush having abundant foliage and propagation of this seedling was done by me at Watsonville, Calif. by use of cuttings with excellent results whereupon, under my direction, this plant was propagated through several successive generations which demonstrated conclusively that the novel characteristics of the selected seedling would hold true from generation to generation and appeared to be firmly fixed.

DESCRIPTION OF THE DRAWING

This new miniature pot rose is illustrated by the accompanying photographic drawing which shows the plant in full color with blooms in several stages of maturity with color rendition as nearly true to that herein specified as is reasonably possible to obtain by conventional photographic procedures.

DESCRIPTION OF THE NEW VARIETY

The following is a detailed description of my new miniature pot rose as observed from greenhouse plants grown at Watsonville and with color designations being according to the R.H.S. Colour Chart published by The Royal Horticultural Society of London, England.

THE PLANT

Origin: Seedling.

Parentage:

*Seed parent.*—An unnamed and unpatented variety selected from the rose plants maintained at Watsonville for breeding purposes.

*Pollen parent.*—An unpatented variety named 'Amber Flash'.

Classification:

*Botanic.*—Hybrid miniature rose.

*Commercial.*—Miniature pot rose.

Form: An upright free branching bush.

Height: About 23 cm. at twelve weeks of growth in a 4 inch pot.

Main stem length: About 168 mm. from the last flower cut.

*Color.*—Yellow Green 144-A.

Growth habit: Vigorous, sturdy and upright.

Branching character: Free branching.

Foliage:

*Quantity.*—Abundant.

*Number of leaves.*—5 or 6, from the last flower cut. Size: About 72 mm. long in average.

Leaflets:

*Number.*—3 or 5.

*Size.*—About 30 mm. long and 18 mm. wide.

*Shape.*—Ovate with denticulate margins.

*Texture.*—Leathery and smooth.

*Color.*—Upper side — Yellow Green 144-A. Under side — Green 138-B.

*Stipules.*—Adnate.

*Rachis.*—About 17 mm. long on a 3 part leaf.

Ribs and veins: Depressed on top side of leaf and protruding on the underside.

Thorns:

*Size.*—About 6 mm.

*Color.*—Greyed Purple 183-A.

THE BUD

Size: Small, mini-flora.

*Diameter.*—About 12 mm.

*Length.*—About 16 mm.

Shape: Somewhat urn shaped.

Rate of opening: Slow.

Color of petals:

*When sepals first divide.*—Cadmium Orange 23-A.

*When petals begin to unfurl.*—23-B.

Sepals:

*Number.*—Five.

*Character.*—Spreading with small leafs protruding on each side and curled back when flower opens.

*Color.*—Inside — Chrome Yellow 14-D. Outside — Scheeles Green 144-B.

Calyx:

*Shape.*—Funnel-shaped.

*Size.*—Small, broad and short in length.

*Splitting.*—Calyx does not split.

*Aspect.*—Smooth.

Peduncle:
*Length.*—About 42 mm.
*Character.*—Slender and erect.
*Color.*—Scheeles Green 144-B.

THE FLOWER

Blooming habit: Continuous and profusely the year around under greenhouse conditions.
Size of bloom: Small.
*Diameter.*—About 40 by 42 mm.
*Depth.*—About 17 mm.
Borne: Singly on strong upright stems.
Shape:
*When bloom first opens.*—Somewhat cup shaped with high center.
*When bloom matures.*—The shape becomes flattened and the petals are regularly imbricated.
Petalage:
*Number.*—48.
*Number of florets.*—14.
*Arrangement.*—Imbricated.
*Form.*—Ovate in general with margins tending to curl under.
*Texture.*—Soft.
*Appearance.*—Velvety.
*Color.*—Outer petals: Upper side body — Tangerine Orange 24-B with base of Lemon Yellow 14-A. Reverse side body — 24-B with base of Lemon Yellow 13-B. Inside petals: Upper side body — Cadmium Orange 23-A with base of Lemon Yellow 13-A. Reverse side body — 24-B with base of Chrome Yellow 16-A.
Petaloids:
*Number.*—14.
*Size.*—About 9 mm. long.
*Color.*—Indian Yellow 17-A with base of 17-C.

Peduncle:
*Length.*—About 42 mm.
*Color.*—Yellow Green 144-B.
*Character.*—Upright and sturdy.
Fragrance: Strong.
Disease resistance: Moderately resistant to mildew, rust and black spots as observed at Watsonville, Calif.
Lasting quality: Long lasting on plant and as a cut flower.

THE REPRODUCTIVE ORGANS

Stamens:
*Number.*—52.
*Arrangement.*—Antrorse.
*Anthers.*—Size: About 2 mm. Color: Yellow Orange 16-B.
*Filaments.*—Length: About 4 mm. Color: Yellow Orange 14-C.
*Pollen.*—Color: Yellow Orange 16-B.
Pistils:
*Number.*—63.
*Styles.*—Length: About 8 mm. Color: Greyed Purple 186-C.
*Stigmas.*—Color: Yellow 4-C.
Character of the ovaries: Slender, long and covered with silvery hairs.

I claim:

1. A new and distinct variety of miniature pot plant rose, substantially as herein shown and described, particularly characterized by its profuse and continuous production of relatively small Cadmium Orange flowers borne singly on strong upright stems of a bush having an average height of about 23 cm. at the age of about twelve weeks as grown in a 4 in. pot.

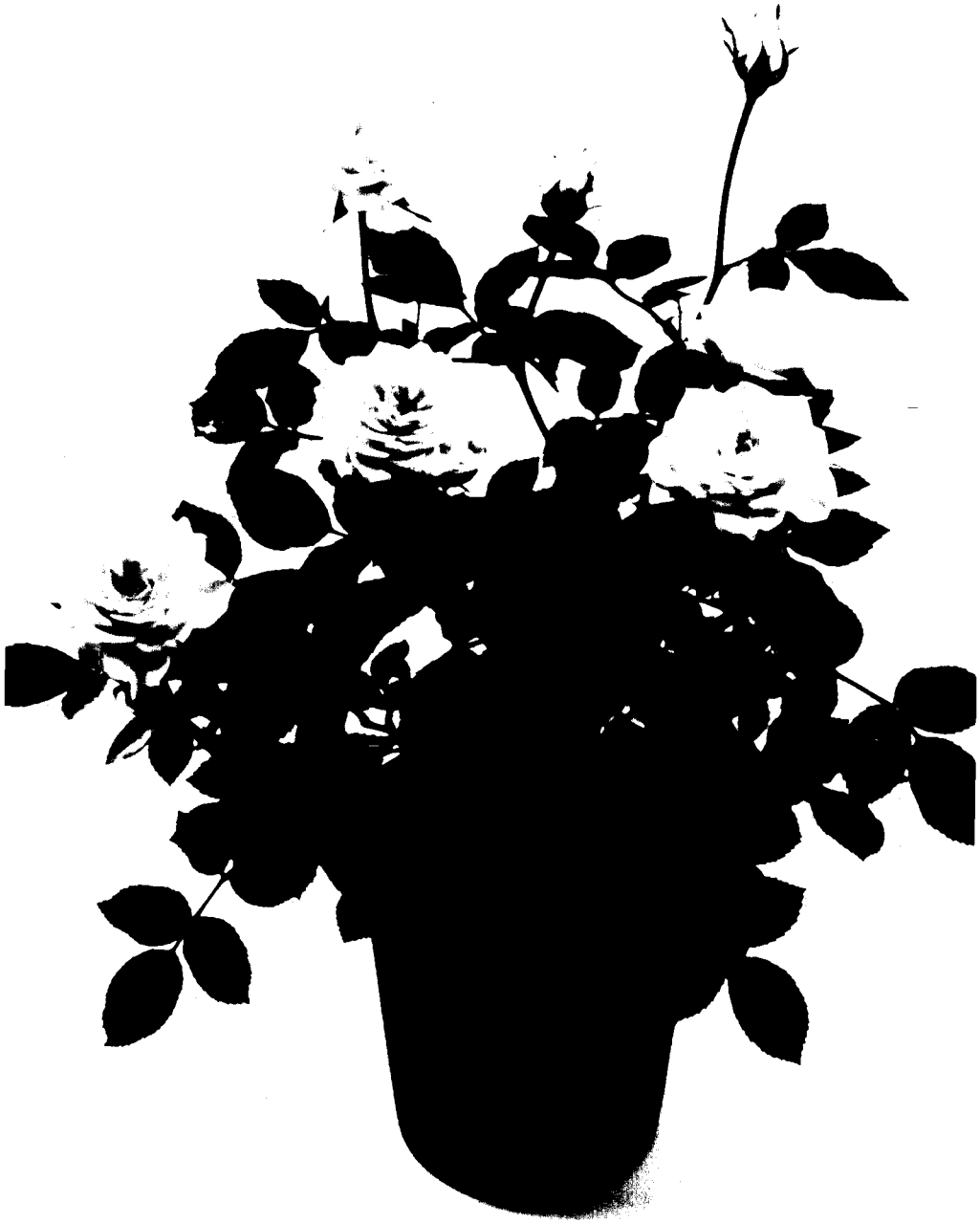

* * * * *